US010011009B2

(12) United States Patent
Bernardi et al.

(10) Patent No.: US 10,011,009 B2
(45) Date of Patent: Jul. 3, 2018

(54) GUIDE FOOT FOR AN OSCILLATING POWER TOOL

(71) Applicants: Robert Bosch Tool Corporation, Broadview, IL (US); Robert Bosch GmbH, Stuttgart (DE)

(72) Inventors: Walter M. Bernardi, Highland Park, IL (US); Daniel Shadegg, Buffalo Grove, IL (US); Dale S. Dilulio, Saukville, WI (US); Scott H. Micoley, Cedarburg, WI (US); Saad Alam, Franklin Park, IL (US); Balazs Nagy, Schaumburg, IL (US); Jaime Moreno Terrazas, Imperial, CA (US); Jeremy Rubens, Palatine, IL (US)

(73) Assignees: Robert Bosch Tool Corporation, Broadview, IL (US); Robert Bosch GmbH, Stuttgart (DE)

(*) Notice: Subject to any disclaimer, the term of this patent is extended or adjusted under 35 U.S.C. 154(b) by 751 days.

(21) Appl. No.: 14/518,339

(22) Filed: Oct. 20, 2014

(65) Prior Publication Data

US 2015/0122526 A1 May 7, 2015

Related U.S. Application Data

(60) Provisional application No. 61/898,649, filed on Nov. 1, 2013.

(51) Int. Cl.
*B24B 55/05* (2006.01)
*B25F 5/02* (2006.01)
(Continued)

(52) U.S. Cl.
CPC .............. *B25F 5/021* (2013.01); *B24B 23/04* (2013.01); *B24B 55/052* (2013.01); *B26B 7/00* (2013.01);
(Continued)

(58) Field of Classification Search
CPC .... B25F 3/00; B25F 5/00; B25F 5/003; B25F 5/021; B23D 47/12; B23D 47/126;
(Continued)

(56) References Cited

U.S. PATENT DOCUMENTS 3,270,785 A * 9/1966 Molitor .................... B27B 9/00
30/293
3,740,847 A * 6/1973 Kliever .................... B26B 7/00
30/277.4
(Continued)

FOREIGN PATENT DOCUMENTS

DE 102006023888 A1 11/2007

*Primary Examiner* — Scott A. Smith
(74) *Attorney, Agent, or Firm* — Maginot Moore & Beck LLP

(57) ABSTRACT

A guide member for an oscillating power tool includes an attachment portion configured to be removably attached to a housing of the power tool and a guide portion that extends from the attachment portion. The guide portion includes a leading edge, a trailing edge, and a guide surface. When the attachment portion is attached to the housing of the power tool, the guide portion is configured to extend beyond the housing in a first direction to position the leading edge portion a predetermined distance apart from the oscillation axis, the predetermined distance being greater than a distance that an accessory tool attached to the power tool extends.

4 Claims, 17 Drawing Sheets

(51) Int. Cl.
*B27B 19/00* (2006.01)
*B24B 23/04* (2006.01)
*B26B 7/00* (2006.01)
*B26B 29/00* (2006.01)
*B24B 23/02* (2006.01)
*A61F 15/02* (2006.01)
*B23D 51/10* (2006.01)

(52) U.S. Cl.
CPC ............ *B26B 29/00* (2013.01); *B27B 19/006* (2013.01); *A61F 15/02* (2013.01); *B23D 51/10* (2013.01); *B24B 23/02* (2013.01); *B24B 55/055* (2013.01)

(58) Field of Classification Search
CPC ........ B23D 51/06; B23D 51/08; B23D 51/10; B24B 23/02; B24B 23/028; B24B 23/04; B24B 55/052; B24B 55/10; B24B 55/055; B27B 5/08; B27B 9/02; B27B 9/006; B27B 19/02; B27B 19/006; A61F 15/02
USPC ............. 173/49, 29, 31, 213, 217, 141, 100; 30/277.4, 293, 371, 373, 390, 39, 133, 30/122, 124, 166.3, 286, 296.1; 451/344, 451/358, 359, 451, 454; 606/82, 178
See application file for complete search history.

(56) References Cited

U.S. PATENT DOCUMENTS

| | | | | |
|---|---|---|---|---|
| 4,361,956 A * | 12/1982 | Kirk | ........................ | A61F 15/02 30/122 |
| 4,411,067 A * | 10/1983 | Kirk | ........................ | A61F 15/02 30/124 |
| 4,543,718 A * | 10/1985 | Duescher | ................ | A61F 15/02 30/124 |
| 4,625,405 A * | 12/1986 | Hudnutt | .................. | A61F 15/02 30/370 |
| 5,440,815 A * | 8/1995 | Inkster | .................. | B24B 55/052 30/390 |
| 5,468,247 A * | 11/1995 | Matthai | .................. | A61F 15/02 30/339 |
| 5,964,039 A * | 10/1999 | Mizoguchi | ........... | B23D 49/165 30/124 |
| 6,048,260 A * | 4/2000 | Kopras | ................ | B24B 23/028 144/154.5 |
| 6,699,114 B1 * | 3/2004 | Booeshaghi | ............. | B23Q 1/52 451/451 |
| 6,878,050 B2 * | 4/2005 | Wendt | ................ | B23Q 11/0046 451/344 |
| 6,918,720 B2 * | 7/2005 | Kopras | ................ | B25H 1/0078 144/136.95 |
| 7,047,650 B2 * | 5/2006 | Chen | ........................ | B27B 5/08 30/373 |
| 7,063,606 B2 * | 6/2006 | Stierle | .................... | B24B 23/02 451/359 |
| 7,077,736 B2 * | 7/2006 | Uzumcu | .............. | B23D 47/126 451/358 |
| 7,596,872 B2 * | 10/2009 | Clarke | .................. | B23D 45/16 30/388 |
| 7,628,683 B2 * | 12/2009 | Hofmann | .............. | B24B 55/052 451/454 |
| 7,955,162 B2 * | 6/2011 | Boeck | .................... | B24B 23/00 451/359 |
| 8,133,094 B2 * | 3/2012 | Loveless | ................ | B24B 55/10 451/28 |
| 8,282,446 B2 * | 10/2012 | Sulea | ...................... | B24B 23/02 451/451 |
| 8,365,419 B2 * | 2/2013 | Bernardi | .................. | B25F 5/00 30/371 |
| 8,523,640 B2 * | 9/2013 | Esenwein | ............. | B24B 23/028 451/359 |
| 8,784,164 B2 * | 7/2014 | Dai | ........................ | B24B 23/02 451/359 |
| 9,149,923 B2 * | 10/2015 | Campbell | ................ | B25F 5/003 |
| 9,186,769 B2 * | 11/2015 | Moncrieff | ............... | B26B 29/00 |
| 9,702,153 B2 * | 7/2017 | Kehoe | .................. | E04F 21/0084 |
| 2003/0070307 A1 * | 4/2003 | Walker | .................... | B23D 51/16 30/374 |
| 2008/0027449 A1 * | 1/2008 | Gundlapalli | ........ | A61B 17/1613 606/82 |
| 2011/0072946 A1 * | 3/2011 | Bernardi | .................. | B25F 5/00 83/522.11 |
| 2011/0314680 A1 * | 12/2011 | Zhang | ........................ | B25F 3/00 30/228 |
| 2012/0211951 A1 * | 8/2012 | Montplaisir | ............ | B24B 23/04 279/141 |
| 2013/0090045 A1 * | 4/2013 | Meyer | .................... | B24B 23/028 451/359 |
| 2013/0126198 A1 * | 5/2013 | Campbell | ................ | B25F 5/003 173/31 |
| 2013/0193655 A1 * | 8/2013 | Kaye, Jr. | .................. | B25F 3/00 279/141 |

* cited by examiner

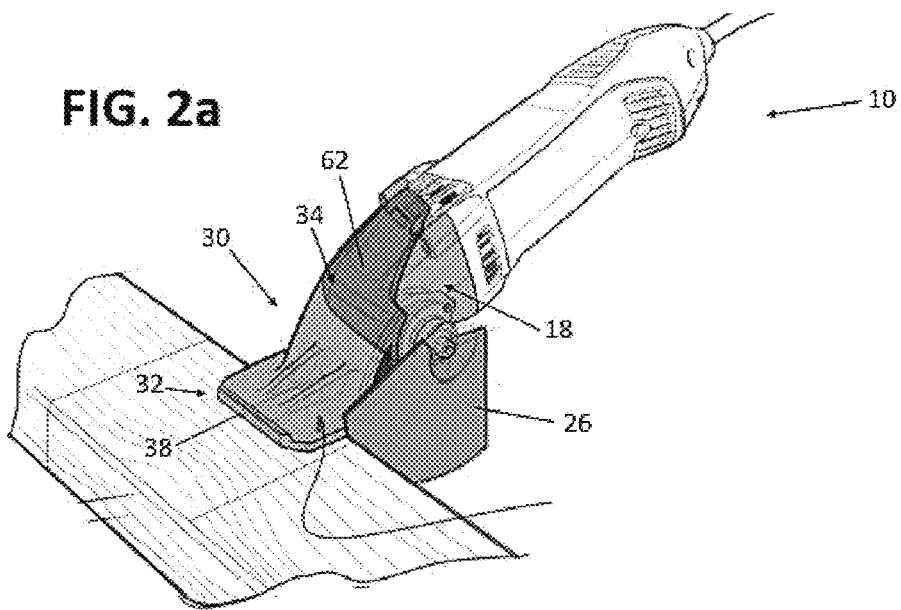
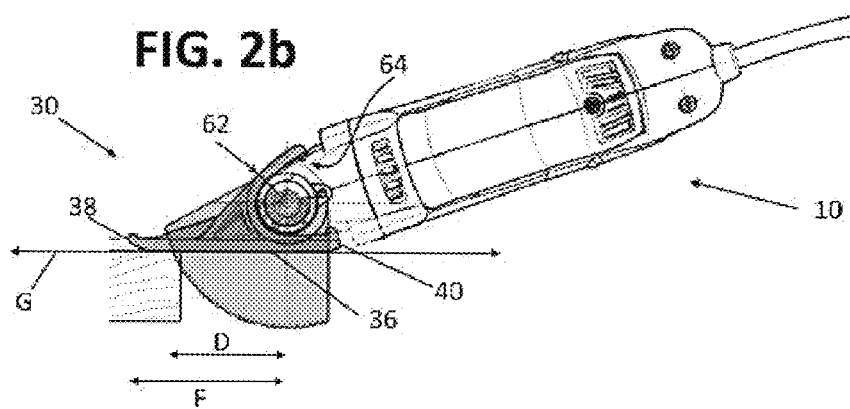
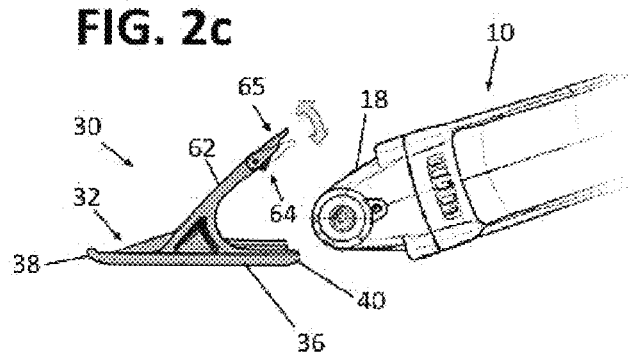

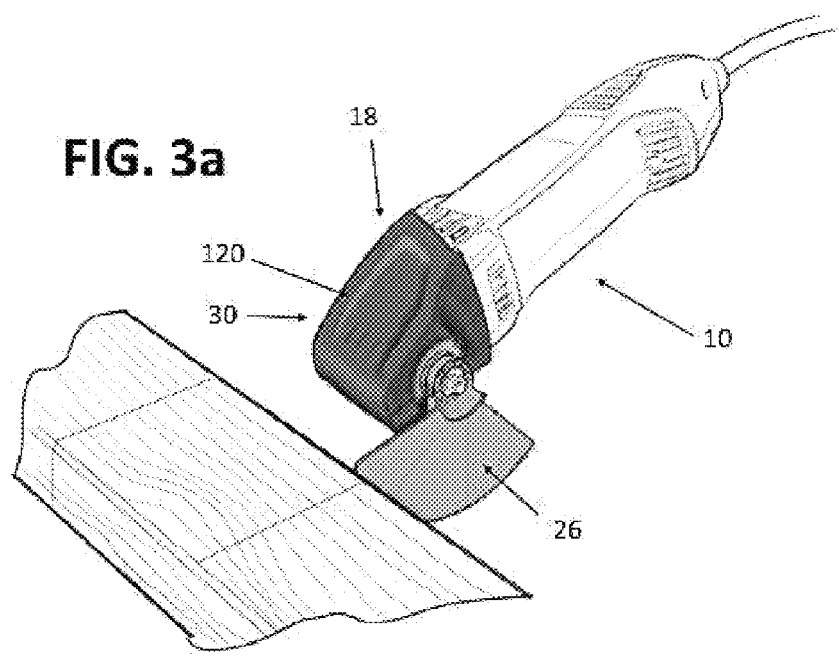
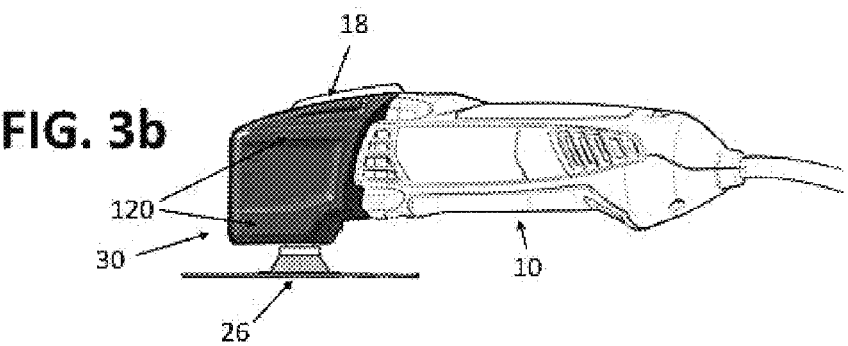
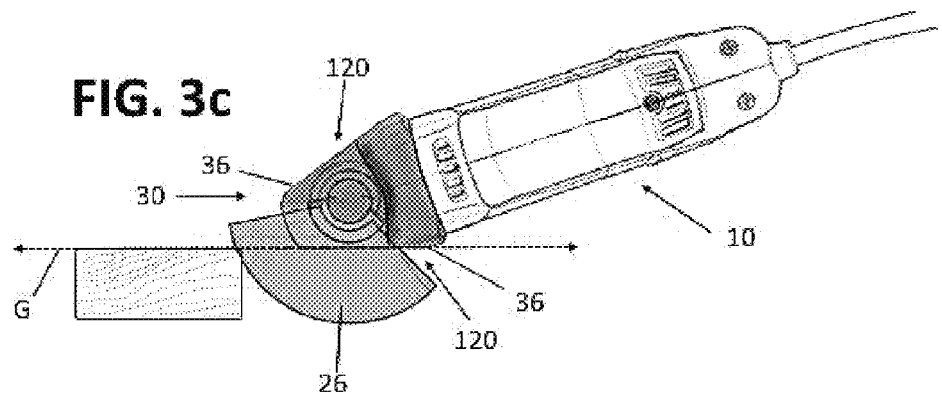

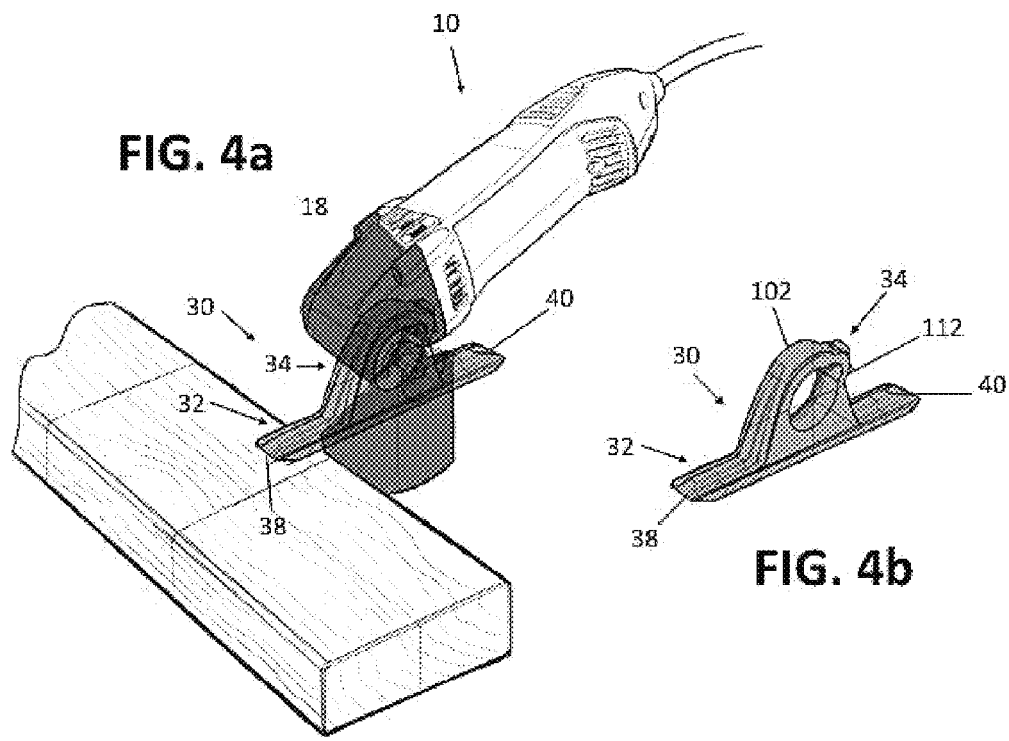
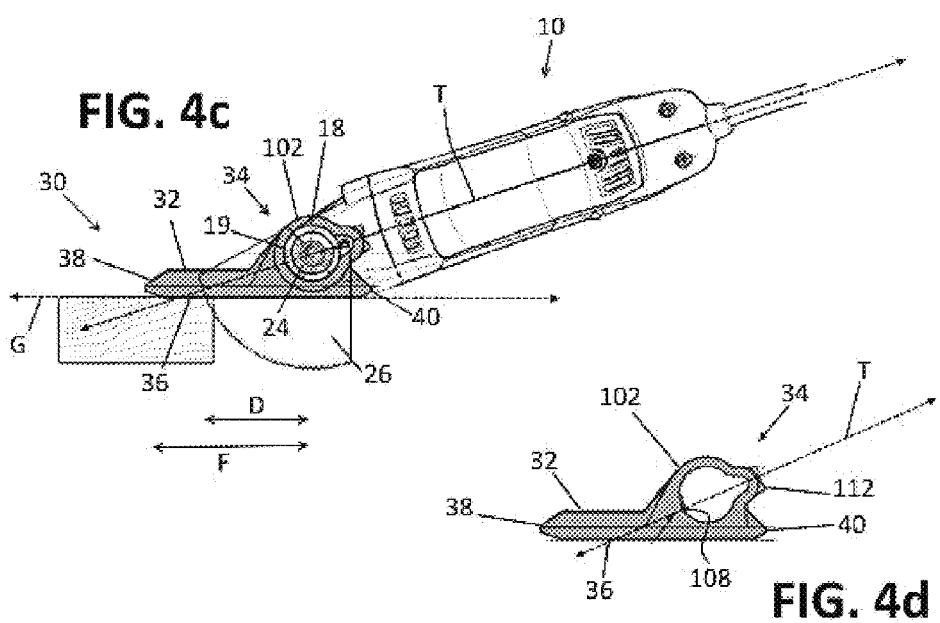

GUIDE FOOT FOR AN OSCILLATING POWER TOOL

CROSS-REFERENCE TO RELATED APPLICATIONS

This application claims priority to U.S. Provisional Application Ser. No. 61/898,649 entitled "GUIDE FOOT FOR AN OSCILLATING POWER TOOL" by Bernardi et al., filed Nov. 1, 2013, the disclosure of which is hereby incorporated herein by reference in its entirety.

TECHNICAL FIELD

This disclosure relates to the field of oscillating power tools, and more particularly to attachments for use with oscillating power tools.

BACKGROUND

In general, oscillating tools are light-weight, handheld power tools capable of being equipped with a variety of tool accessories and attachments, such as cutting blades, sanding discs, grinding tools, and many others. These types of tools typically include a generally cylindrically-shaped main body that serves as an enclosure for an electric motor as well as a hand grip for the tool. The electric motor oscillates a tool holder to which any one of various accessory tools may be attached. As the tool holder is oscillated, an accessory tool attached to the tool holder is driven to perform a particular function, such as sanding, grinding, or cutting, depending on the configuration of the accessory tool.

Accessory tools for an oscillating power tool typically have one-piece rigid construction that includes a mounting portion that is used to secure the accessory tool to the tool holder and a tool body extending from the mounting portion that supports a working portion of the accessory tool, such as an abrasive surface or sharp edge. The tool holder of most oscillating power tools includes a tool drive structure that facilitates a secure and rigid connection between the tool holder and the mounting portion of one or more accessory tools. The accessory tools for use with a power tool are provided with an accessory drive structure configured to interlock with the tool drive structure of the corresponding tool holder. The interlocked drive structures enable the accessory tool to be moved with the tool holder while preventing slippage and other relative movement of the accessory tool with respect to the tool holder as the tool holder is oscillated.

BRIEF DESCRIPTION OF THE DRAWINGS

FIGS. 2a-2e depict a second embodiment of a guide foot for an oscillating power tool.

FIGS. 3a-3c depict a third embodiment of a guide foot for an oscillating power tool.

FIG. 4a-4g depict a fourth embodiment of a guide foot for an oscillating power tool.

DESCRIPTION

Figure 1A:
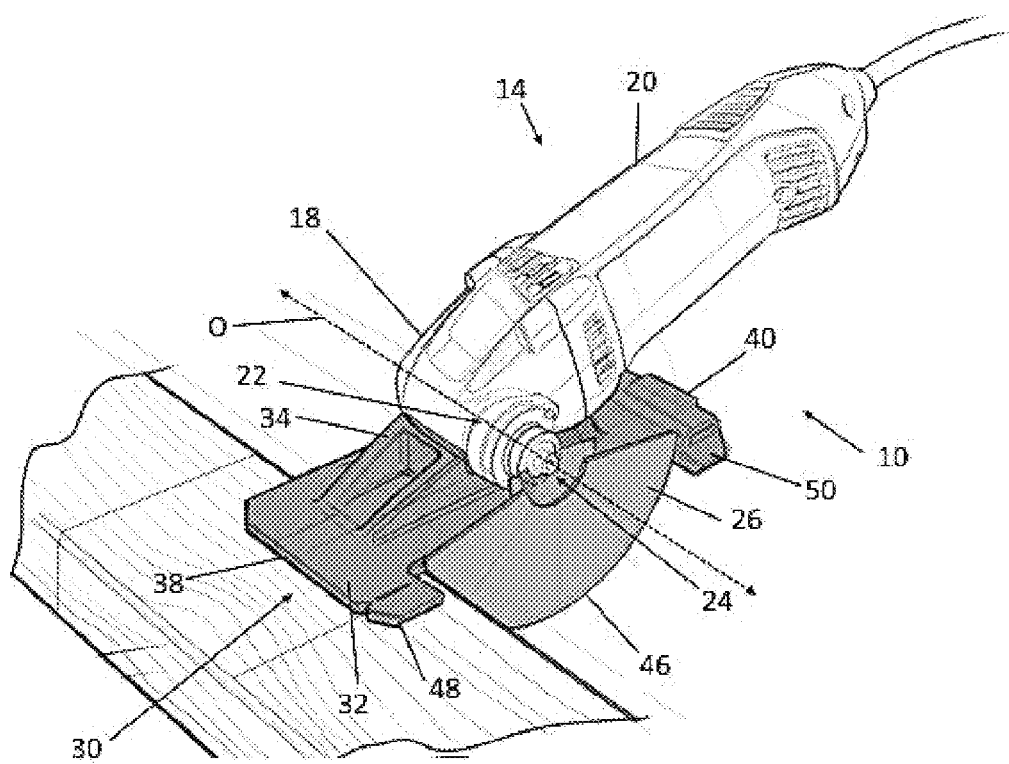
FIGS. 1a-1e depict a first embodiment of a guide foot for an oscillating power tool.

For the purposes of promoting an understanding of the principles of the disclosure, reference will now be made to the embodiments illustrated in the drawings and described in the following written specification. It is understood that no limitation to the scope of the disclosure is thereby intended. It is further understood that the disclosure includes any alterations and modifications to the illustrated embodiments and includes further applications of the principles of the disclosure as would normally occur to one of ordinary skill in the art to which this disclosure pertains.

The disclosure is directed to guide shoes for oscillating power tools that can be attached to or integrated onto oscillating power tools and that enable various advantages over previously known oscillating tools. For example, the guide shoes disclosed herein add stability and accuracy to an oscillating tool especially when making long straight cuts in targets, such as wood, concrete, stone, pipe, tile, glass, composite materials, metal, or the like. The guide shoes can make it easier to follow straight line indicators, such as marked lines, laser lines, and the like, when making cuts. The guide shoes can also improve the control of the depth of cut. The improved stability and control will also allow a user to make faster cuts so work projects can be performed in less time.

According to one embodiment, a power tool is provided that includes a housing having a nose portion, a motor supported within the housing, and an oscillating drive assembly coupled to the motor and configured to be driven to oscillate by the motor. A tool holder is secured to the oscillating drive assembly and located exterior to the housing. The tool holder is configured to removably retain an accessory tool so that the accessory tool is oscillated about an oscillation axis by the oscillating drive assembly. The accessory tool includes an outer edge portion and is configured to extend beyond the nose portion of the housing in at least a first direction that is perpendicular to the oscillation axis to position the outer edge portion a first distance from the oscillation axis.

A guide member is attached to the housing. The guide member includes a leading edge portion, a trailing edge portion, and a guide surface that extends between the leading edge portion and the trailing edge portion. The guide member is configured to extend beyond the nose portion of the housing in the first direction to position the leading edge portion a second distance apart from the oscillation axis that is greater than the first distance. The guide surface is configured to be placed in contact with a surface of a workpiece and defines a guide plane that is substantially parallel to the oscillation axis.

In various embodiments, the guide member is removably attached to the housing. The guide member may have a snap fit, press fit, or other type of non-fastener type attachment mechanism for removably attaching to the housing of the power tool. The guide member may also extend in a second direction that is opposite the first direction to position the trailing edge a third distance apart from the oscillation axis that is greater than the first distance.

The accessory tool defines an oscillation plane in which a working portion of the accessory tool is configured to oscillate, the oscillation plane being perpendicular to the oscillation axis. In one embodiment, the guide member defines a cutout portion between the leading and trailing edge portions that is configured to allow at least a portion of the accessory tool to extend therethrough when the accessory tool is retained by the tool holder. In this embodiment, the oscillation plane and at least one of the leading and trailing edge portions of the guide member is intersected by the oscillation plane.

The guide member may include a movable portion that includes the leading edge portion and at least a portion of the guide surface. The movable portion is configured to move between a first position and a second position in relation to the housing. In one embodiment, the leading edge portion of the guide member is located at a first position in relation to the nose portion of the housing when the movable portion is in the first position and located at a second position in relation to the nose portion of the housing when the movable portion is in the second position.

The movable portion may be configured to pivot with respect to the nose portion of the housing between the first position and the second position. Alternatively, the movable portion may be configured to translate with respect to the nose portion of the housing between the first position and the second position.

In one embodiment, the guide member is configured to be attached at a first position on a first lateral side of the nose portion of the housing and at a second position on second lateral side of the nose portion that is opposite from the first lateral side. The guide surface faces away from the housing when the guide member is attached at both the first position and the second position, and the guide plane is parallel to the oscillation axis when the guide member is attached at both the first position and the second position. This allows versatility in the orienting the tool during use as situations may require.

In another embodiment, the guide member includes a collar portion that is configured to be rotatably attached to the nose portion of the housing. The collar portion is configured to be selectively rotated with respect to the nose portion about the oscillation axis to a plurality of angular positions with respect to the oscillation axis. In this embodiment, the guide member includes a locking mechanism for releasably locking the collar portion at any one of the plurality of angular positions. The locking mechanism may comprise a spring-loaded button, or similar type of structure, that is configured to move a key on the collar into and out of engagement with recesses in the nose portion of the housing that define the plurality of angular positions.

In yet another embodiment, the guide member includes a housing attachment portion and a guide portion. The housing attachment portion is configured to be removably attached to the housing and is also pivotably attached to the guide portion. The guide portion includes the leading edge portion, the trailing edge portion, and the guide surface. The housing attachment portion is configured to pivot between a first position and a second position in relation to the guide portion. In the first position, the oscillation axis is a first distance from the guide plane, and, in the second position, the oscillation axis is a second distance from the guide plane. This configuration adds a plunging capability to the oscillating tool.

A guide member, or guide foot, for an oscillating power tool may take a variety of forms. A first embodiment of a guide foot for an oscillating power tool is depicted in FIGS. 1a-1e. The oscillating tool 10 includes a generally cylindrically shaped housing 14 constructed of a rigid material such as plastic, metal, or composite materials such as a fiber reinforced polymer. The housing 14 includes a nose portion 18 and a main body portion 20. The main body portion 20 serves as the handle for the tool 10 and encloses a motor (not shown). In one embodiment, the motor comprises an electric motor configured to receive power via a power cord (not shown) or a rechargeable battery (not shown). In other embodiments, electric power to the motor may be received from an AC outlet via the power cord. As an alternative to electric power, the tool may be pneumatically driven, fuel powered, such as gas or diesel, or hydraulically powered. Power to the motor is controlled by an input device (not visible) provided either on the main body portion 20 of the housing 14 or the nose portion 18. The input device can be a power switch, a touch switch, a joystick switch, a sensing switch, a pressure switch, a touch screen, a gesture screen, or the like.

The motor is coupled to an oscillating drive assembly 22 that extends from the nose portion 18 of the housing 14. The oscillating drive assembly 22 supports an accessory tool holder 24 exterior to the nose portion 18 of the housing 14. The tool holder 24 is configured to releasably secure various accessory tools to the drive, such as the cutting blade accessory tool 26. As the tool holder 24 is oscillated by the drive 22, the accessory tool 26 is driven to oscillate about an oscillation axis O.

The oscillating tool 10 is provided with a guide foot 30 that is attached to and/or integrated into the nose portion 18 of the housing. As discussed below, the guide foot may be provided in a variety of configurations. Each guide foot 30 has a guide surface 36 that defines a guide plane G (FIG. 1d) and is configured to be placed in contact with a surface of a workpiece that is being cut and to slide smoothly across the surface of the workpiece when making cuts while maintaining the cutting blade of the tool at a fixed orientation relative to the workpiece.

In the embodiment of FIGS. 1a-1e, the guide foot 30 is provided as an attachment that is configured to be removably attached to the nose portion 18 of the oscillating tool housing in a stationary, non-rotating position relative to the nose and the blade of the tool. The guide foot 30 includes a foot portion 32 and an attachment portion 34. A guide surface 36 is on one side of the foot portion 32 and the attachment portion 34 is provided on the other side of the foot portion. The foot portion 32 is generally planar with a leading edge 38, a trailing edge 40, an inner lateral edge 42, and an outer lateral edge 44. The leading and trailing edges 38, 40 are arranged generally perpendicular to the plane of the cutting blade and the lateral edges 42, 44 are arranged generally parallel to the plane of the blade 26.

Figure 1B:
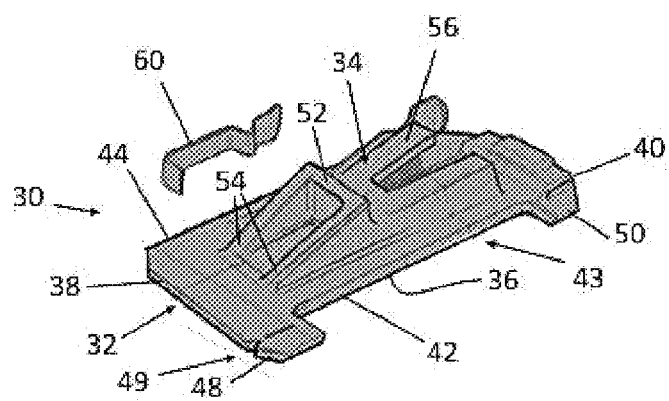
Figure 1C:
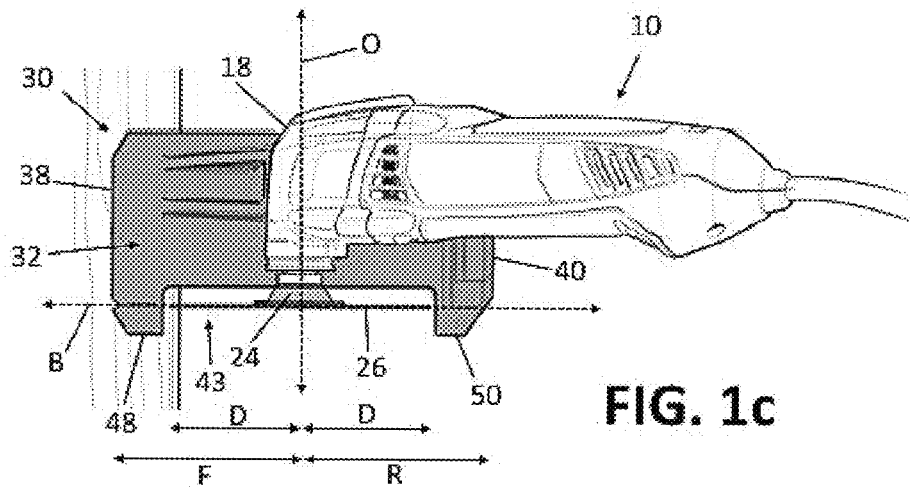
Figure 1D:
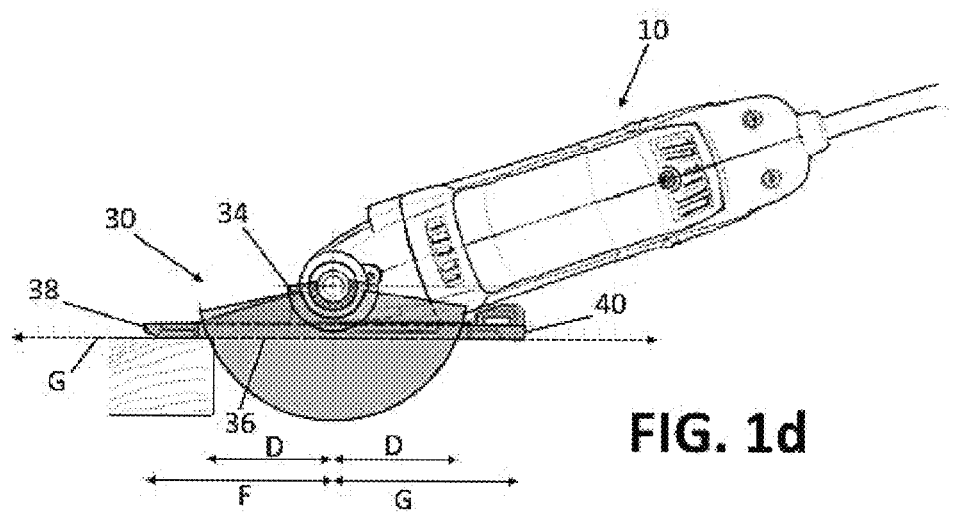
Figure 1E:
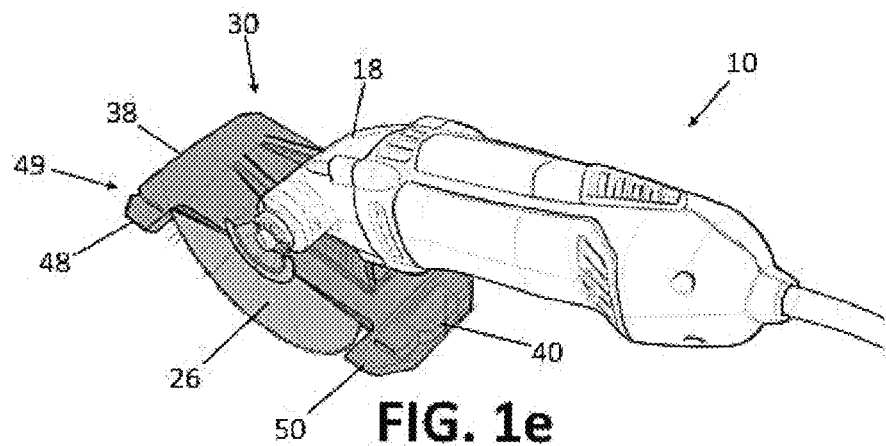

The attachment portion 34 is configured to removably secure the guide foot to the nose portion 18 of the tool with the leading edge 38 of the guide foot positioned in front of the cutting edge 46 of the blade. As can be seen in FIGS. 1c and 1d, the blade 26 is configured to extend a distance D from the oscillation axis O in at least one direction that is perpendicular to the oscillation axis O. The guide portion 32 is configured to extend in the forward direction to position the leading edge 38 a distance F from the oscillation axis with the distance F being greater than the distance D. This allows the tool to be positioned and supported in its proper cutting orientation before the blade engages the workpiece to start the cut. The leading edge of the guide portion is positioned in front of the leading edge of the blade in each of the embodiments described below except for the embodiment depicted in FIGS. 3a-3c in which the guide is fully integrated into the housing of the tool so that the forward extension of the guide is limited due to design constraints.

In the embodiment of FIGS. 1a-1e, the guide portion 32 is also configured to extend rearwardly to position the trailing edge 40 a distance G from the oscillation axis with the distance G being greater than D as well. The distances G and F may be the same although not necessarily. In other embodiments, the trailing edge need not extend rearwardly beyond the trailing edge of the blade.

The guide foot 30 may include extensions 48 and 50 that protrude laterally from the guide foot in front of and behind the blade 26. In particular, the leading edge 38 includes an extension 48 that extends laterally from the foot portion in front of the cutting edge 46 of the blade 26, and a trailing edge extension 50 that extends laterally from the foot portion behind the cutting edge of the blade. The extensions 48, 50 define a cutout region (43, FIGS. 1b, 1c) therebetween through which the blade 26 extends when it is attached to the tool holder. The plane B of the blade intersects the cutout region 43 and the front and rear extensions 48, 50. The leading edge extension and trailing edge extension may be provided with markings 49, such as lines and/or notches, that are aligned with the plane of the blade 26 for indicating the cut line.

The attachment portion 34 includes a front support portion 52 that is held against the nose portion 18 of the tool housing when the guide foot 30 is attached to the tool. The nose portion 18 is pushed against the front support portion 52 as the user moves the blade into engagement with the workpiece. Ribs 54 may be used to strengthen the structure of the guide foot between the front support and the foot portion of the guide foot. In another embodiment, the nose portion 18 can be sited firmly in a pocket (not shown) formed between the ribs 54. The pocket mated with the contour of the nose portion. The pocket can extend into the attached portion 34.

In one embodiment, the attachment portion 34 is configured to have a dovetail type engagement with the nose portion 18 of the tool housing to removably secure the guide foot to the tool. The dovetail attachment mechanism holds the guide foot in a fixed, non-rotating position with respect to the tool housing. Although a dovetail type engagement is described, the actual shape of the engagement portions need not be exactly dovetail-shaped and can be any suitable shape that enables retention in the manner of a dovetail type joint as is known in the art.

The attachment portion 34 of the guide includes a dovetail-shaped rail 56 that extends upwardly from the guide foot. The nose portion 18 of the tool housing is provided with a complementarily-shaped dovetail slot 58 (e.g., FIG. 2e) or groove that is configured to receive the rail 56 on the guide foot. The rail 56 on the guide foot slides into the slot 58 in the nose 18 of the tool from the front which is the same direction the tool will be moved by the user during use. The rail is slid into the slot in the nose of the housing until the nose portion reaches the front support of the guide foot.

A catch mechanism may be incorporated into the guide foot 30 to enable the guide foot to be retained on the tool. As depicted in FIG. 1b, the catch mechanism 60 may comprise a spring mechanism (shown removed) having a detent structure that is configured to engage a complementary detent structure (not shown) provided on the nose housing 18. The catch mechanism can be pressed, for example, to disengage the catch so the guide foot can be removed from the nose of the tool housing.

Figure 2D:
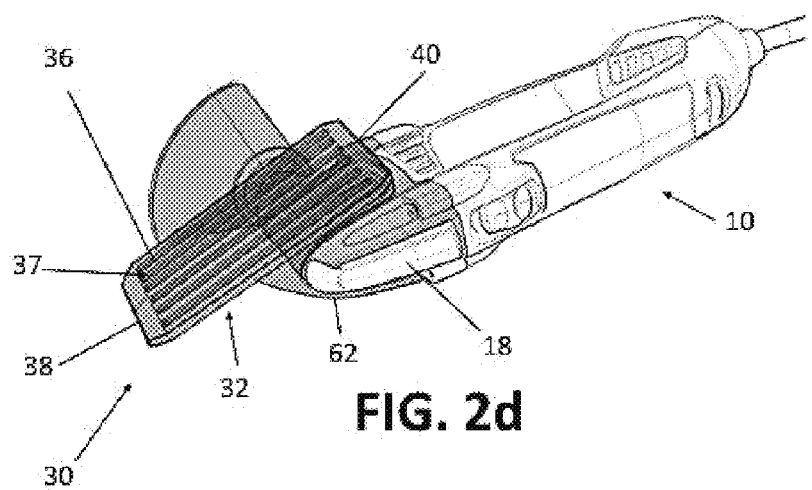
Figure 2E:
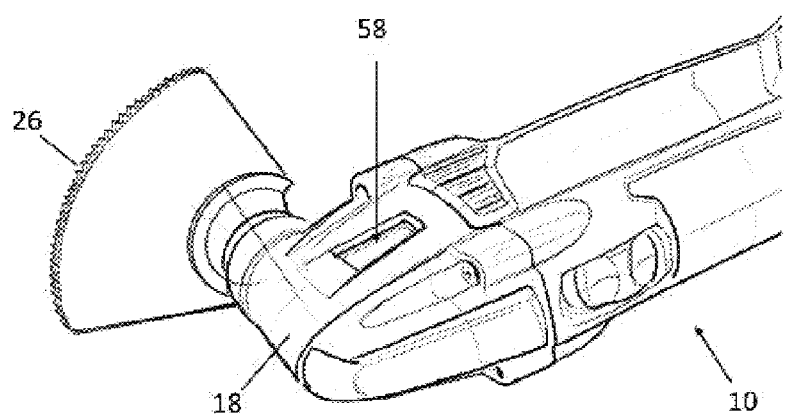
Figure 4E:
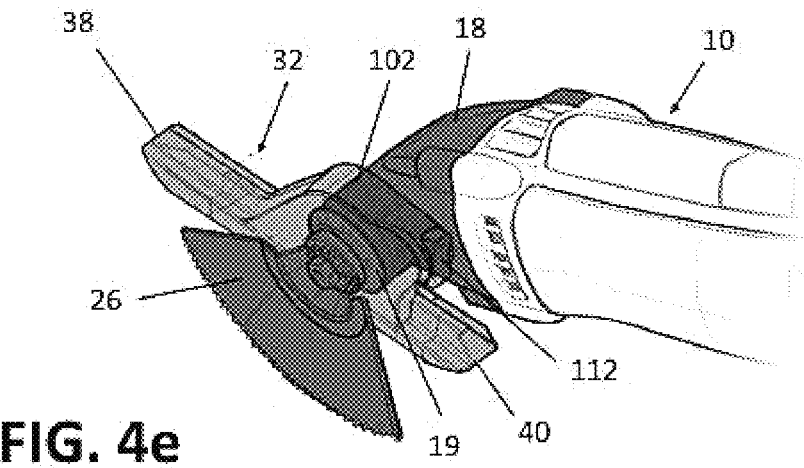
Figure 4F:
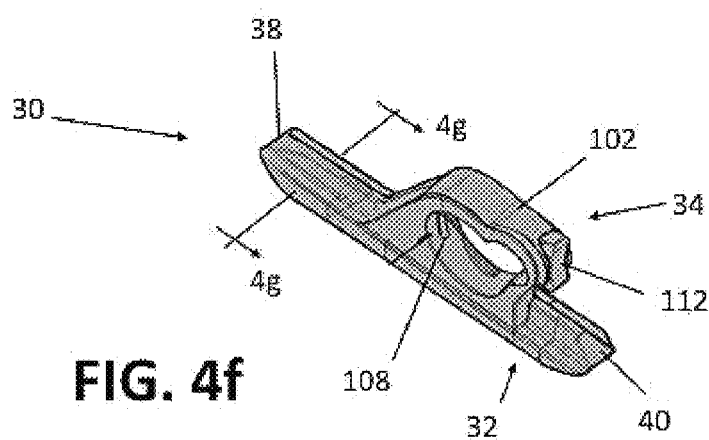
Figure 4G:
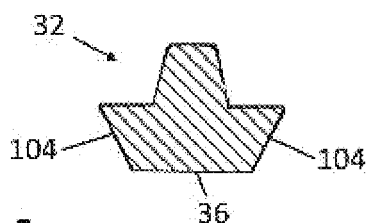

The embodiment of the guide foot of FIGS. 1a-1e is a removable guide foot that is configured to be attached in a fixed, stationary position on the housing of the tool 10. FIGS. 2a-2e and FIGS. 3a-3c depict other embodiments of a stationary guide foot. The embodiment of the guide foot 30 of FIGS. 2a-2e the attachment portion 34 has a snap on or press on configuration enabled by an upper extension portion 62 that extends around the front of the nose portion 18. The extension 62 includes detents 64 (FIG. 2b) that are configured to have a snap fit or press fit engagement with complementary structure 58 provided on the housing 18. As depicted in FIG. 2c, the attachment portion 34 may include a lever mechanism 65 that is configured to move the detent structure 64 into and out of engagement with the corresponding structure on the nose portion 18 of the housing.

The guide portion 32 of the guide member may include various features to facilitate movement of the guide surface 36 against the surface of a workpiece. For example, the leading edge 38 may have a rounded contour as depicted in FIGS. 2b and 2c. As another example, the bottom guide surface 36 may be provided with grooves 37 as depicted in FIG. 2d to facilitate a smooth movement over the surface of the workpiece. These features are not exclusive to the embodiment of FIGS. 2a-2e and may be incorporated into any of the embodiments described herein.

FIGS. 3a-3c depict another embodiment of an oscillating power tool having a guide structure 30. In this embodiment, the guide structure 30 is fully integrated into the nose portion 18 of the housing. As can be seen in FIGS. 3a-3c, the integrated guide structure 30 comprises planar glide surfaces 120 formed on one or both sides of the housing 18. In one embodiment, the glide surfaces 120 are formed by angled walls or ridges that project from the sides of the nose portion 18 of the housing to define a raised ramp structure with a flat outer surface provided at a suitable angle to facilitate placement against a surface of a workpiece. The raised glide surfaces 120 may be provided on a single side, or on both sides of the nose of the housing 18 as can be seen in FIG. 3c.

In one embodiment, the glide surfaces 120 are incorporated into the clamshell housing parts that form the nose portion of the tool. The nose portion 18 of the housing may be extended to provide adequate surface area for supporting the tool during cutting operations. The integrated guide structure 30 of FIGS. 3a-3c does not require handling of an extra part. However, the leading edge of the guide structure 18 is limited by mechanical constraints although the limited extension facilitates the incorporation of the glide surfaces on both sides of the housing.

Referring to FIGS. 4a-4g, an embodiment of a guide foot is depicted that is configured to be mounted at two different orientations with respect to the housing which enable the tool to be used with the housing oriented in either direction. In this embodiment, the guide portion 32 of the guide member has a narrow ski-like configuration with a flat guide surface 36 for guiding normal cuts. The guide portion also has beveled edges that form beveled guide surfaces 104 (FIG. 4g) that can be used for guiding beveled cuts.

The guide member includes an attachment portion 34 that comprises a collar 102. The collar 102 is configured to fit around the neck portion 19 (FIG. 4c) of the tool 10 adjacent the tool holder 24. The collar 102 defines an opening with a predetermined peripheral shape. The neck portion 19 of the tool 10 is provided with an outer perimeter that is shaped complementary to the periphery of the opening to enable the collar portion 102 to be installed by aligning the peripheral shapes of the opening and the neck so that the neck can be inserted through the opening until the collar portion is situated around the neck portion 19 above the tool holder 24.

To enable the guide member to be installed onto the neck at two different orientations, the opening in the collar 102 and the peripheral shape of the neck 19 each have an irregular shape that is symmetrical about the tool axis T. This enables the collar portion 102 to be installed with the guide surface 36 facing in either direction which in turn allows the guide to be used with tool 10 oriented in either direction. The guide portion 32 is attached to the collar portion 102 at an orientation that enables the guide surface 36 to form a suitable angle for guiding cuts in both mounting positions.

The collar portion 102 includes a locking mechanism that enables the collar to be releasably secured onto the neck when mounted. In one embodiment, the locking mechanism comprises a spring-loaded projection that protrudes into the opening from the inner wall of the collar portion 102. The projection is configured to extend into a groove provided on the neck portion 19. To install and remove the guide member, an actuator, such as a button 112, may be provided that is configured to retract the key 108 so the collar 102 can be removed from the neck of the tool.

Referring now to FIGS. 5a-5g, an embodiment of a guide member is depicted that is capable of movement with respect to the housing without having to remove the guide member from the tool. The guide member 30 includes a guide portion 32 that is movably attached to the attachment portion 34. In FIGS. 5a-5g, the guide portion is configured for pivotal movement with respect to the housing which results in a "flip out" configuration for the guide that enables the guide foot to be folded backward toward the nose for storage and to be extended, i.e., flipped out, to provide a guide surface for the blade 26. In alternative embodiments, other types of movement may be used including translating movement, such as described below in connection with FIGS. 7a-7e and FIGS. 8a-8c.

Figure 5A:
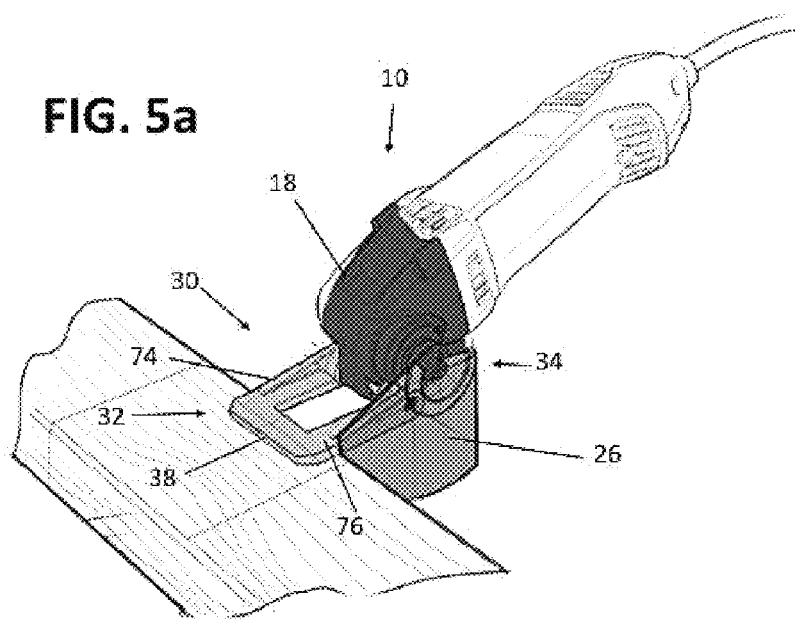
FIG. 5a-5g depict a fifth embodiment of a guide foot for an oscillating power tool.
Figure 5B:
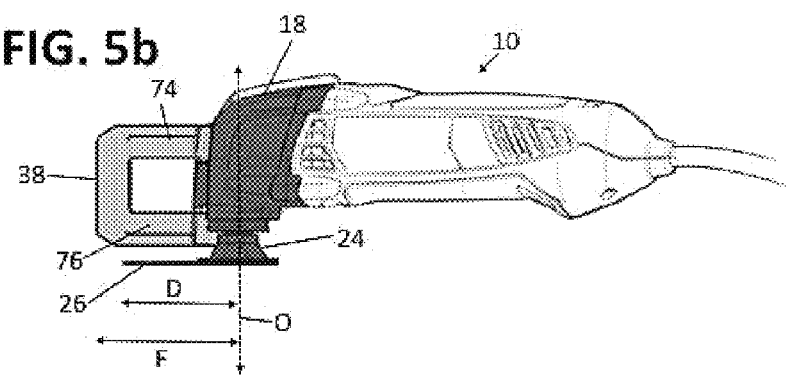
Figure 5C:
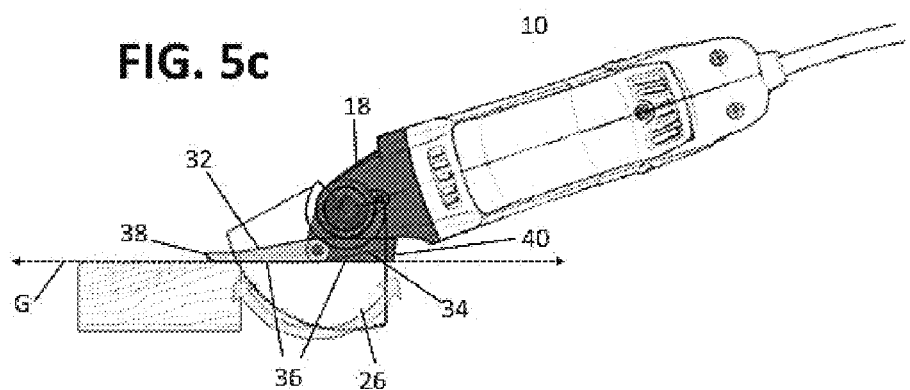
Figure 5D:
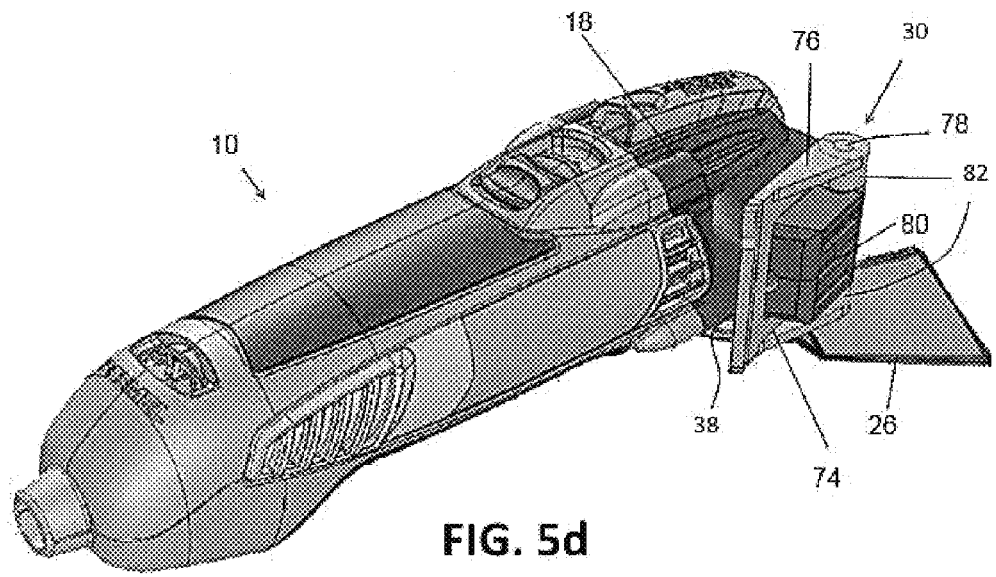
Figure 5E:
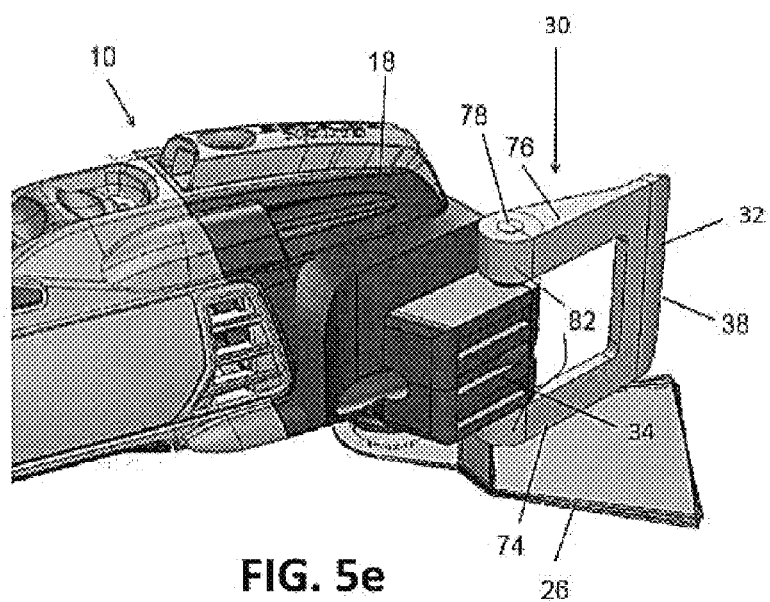
Figure 5F:
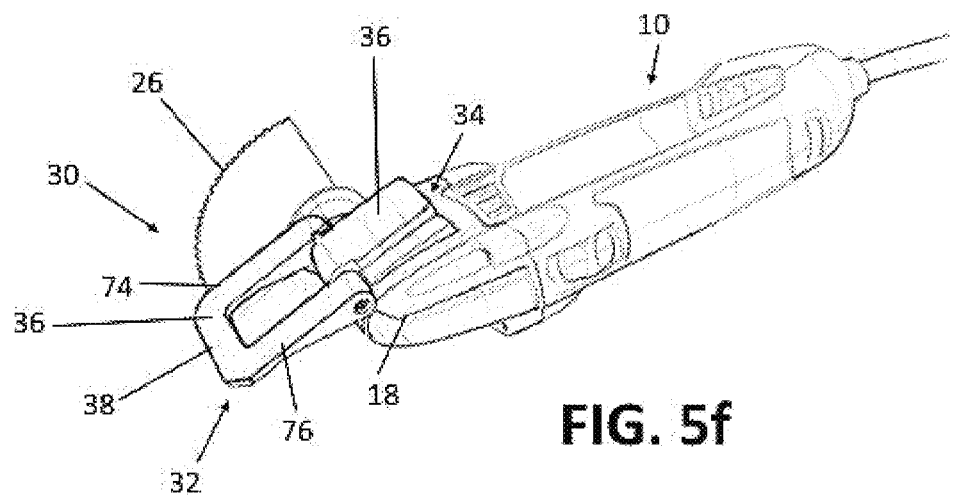

The guide portion 32 includes a leading edge portion 38 that is pivotably attached to the attachment portion 34 by arms 74, 76. The pivot arms may be pivotably supported by a pivot axle 78. The arms 74, 76 are configured to pivot from a stored or retracted position as depicted in FIG. 5d to an extended position as depicted in FIG. 5e. As can be seen in FIG. 5d, the leading edge portion 38 is folded back approximately adjacent to the side of the housing so that the guide member 30 will not interfere with operation of the tool 10. In FIG. 5e, the leading edge portion is located at the distance F so that it is in front of the leading edge of the blade 26. In this embodiment, the attachment portion includes a portion of the guide surface 36 and the leading edge portion, as well as the arms 74, 76 define the remaining portions of the guide surface which are aligned in the extended position.

In FIGS. 5a-5g, the pivotable portion 32 forms a U-shape. In alternative embodiments, other shapes and configurations for the pivotable portion are possible. In one embodiment (not shown), the pivotable portion is separated into left and right sections that are each separately and independently pivotable with respect to the housing. This configuration would enable one side of the guide to be pivoted in one direction and the other side to be pivoted in the other direction to provide a narrower guide surface.

Figure 5G:
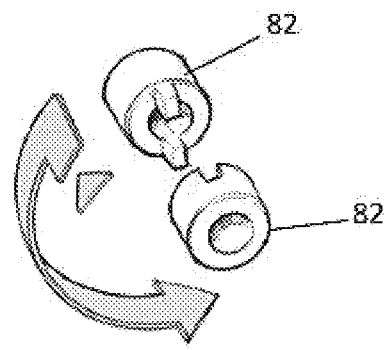

The guide member includes a locking mechanism that enables the guide foot to be releasably locked in the extended position. In one embodiment, the locking mechanism is provided by locking pivot structures 82 on the inner ends of the arms 74, 76 that receive each end of the pivot axle 78. As depicted in FIG. 5g, the locking pivot structures may comprise a 180° military locking pivot. The locking pivot structures 82 have protrusions and recesses that are spring loaded into engagement with complementary recesses and protrusions (not shown) in the surfaces around the pivot axle 78. The guide member must be shifted laterally to disengage the locking pivots 82 so the guide foot can be folded into the stored position (FIG. 5d).

Figure 6A:
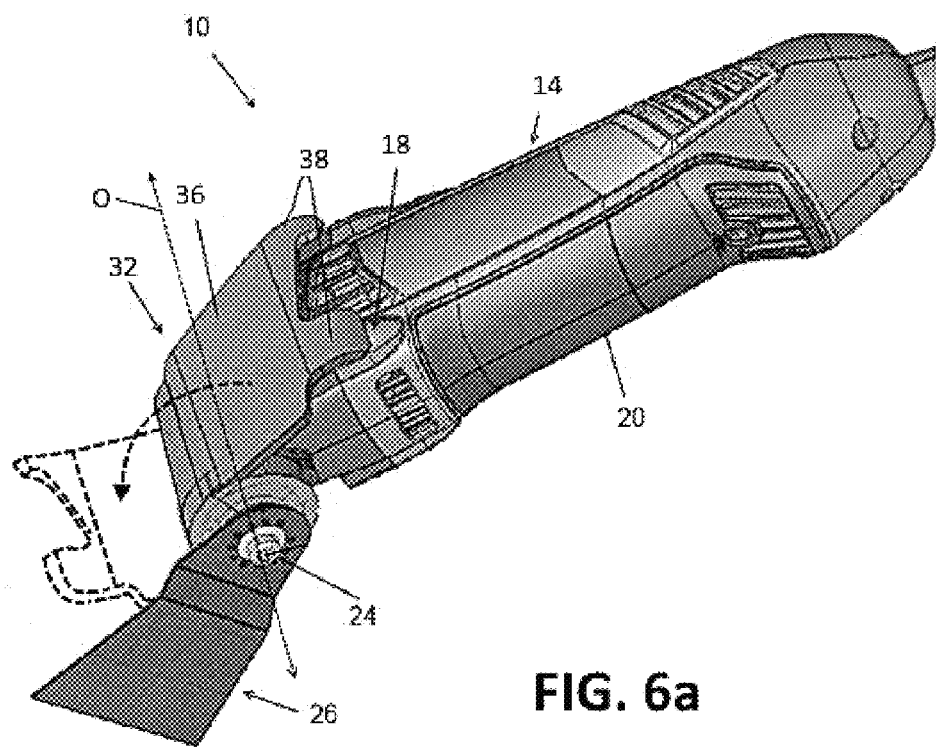
FIGS. 6a-6c depict a sixth embodiment of a guide foot for an oscillating power tool.
Figure 6B:
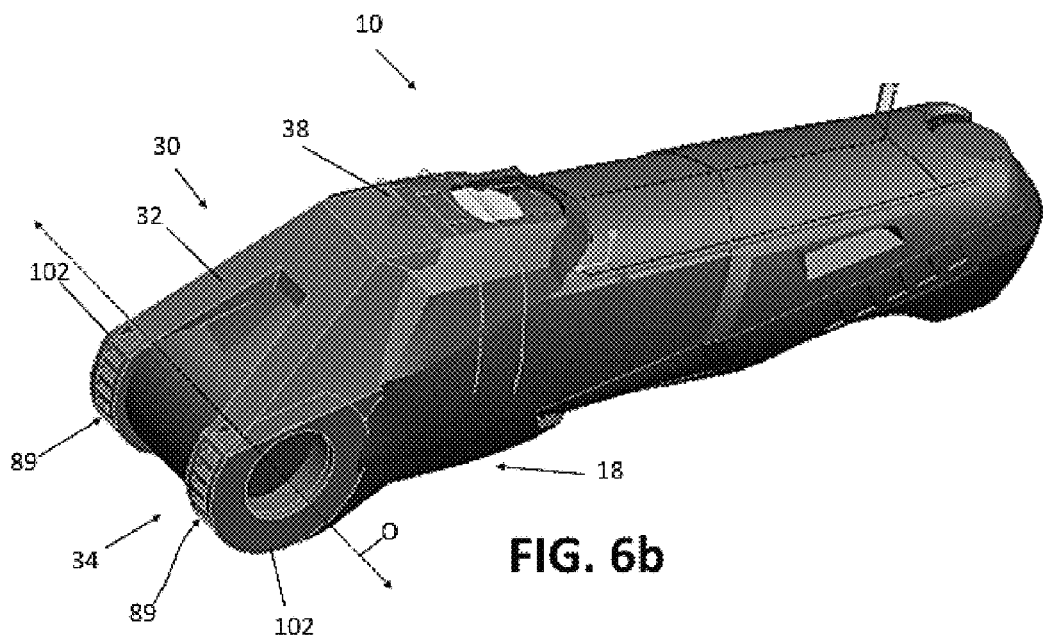
Figure 6C:
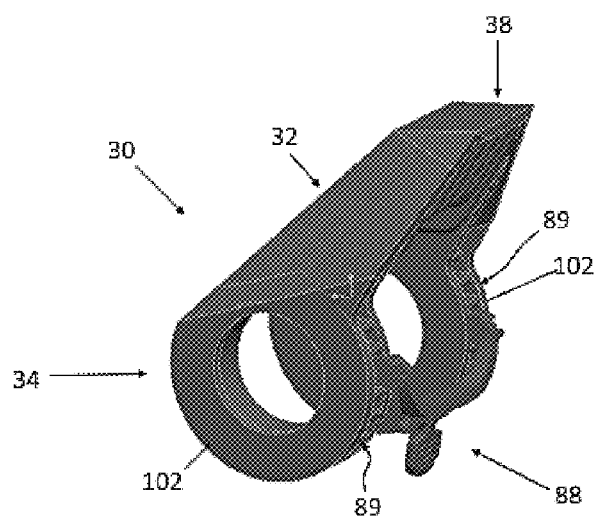

FIGS. 6a-6c depict another embodiment of a guide member that is configured for pivotal movement with respect to the housing. In the embodiment of FIG. 6a-6c, the guide portion 32 is pivotably attached to the nose portion 18 of the housing and is configured to pivot with respect to the housing between a stored position (as shown in FIG. 6a, 6b) and an extended position (indicated by the dotted lines in FIG. 6a). In this embodiment, the guide portion 32 is configured to pivot about the oscillation axis O. As depicted in FIGS. 6b and 6c, the guide member 30 includes at least one collar portion 102 that is configured to be rotatably attached to the nose portion of the housing. Two collar portions 102 are provided for the embodiment of FIGS. 6b and 6c. The collar portions 102 are configured to be selectively rotated with respect to the nose portion 18 about the oscillation axis O to a plurality of angular positions with respect to the oscillation axis O. A locking mechanism 88 for releasably locking the collar portions at any one of the plurality of angular positions is shown in FIG. 6c. The locking mechanism 88 may comprise a spring-loaded button, or similar type of structure, provided on the housing 18 that can be manipulated by a user to move a pawl or key structure into and out of engagement with recesses 89 in the collar portions 102 of the guide member. In alternative embodiments, any suitable method or mechanism may be used to selectively position the guide member at different angular positions with respect to the housing.

Figure 7A:
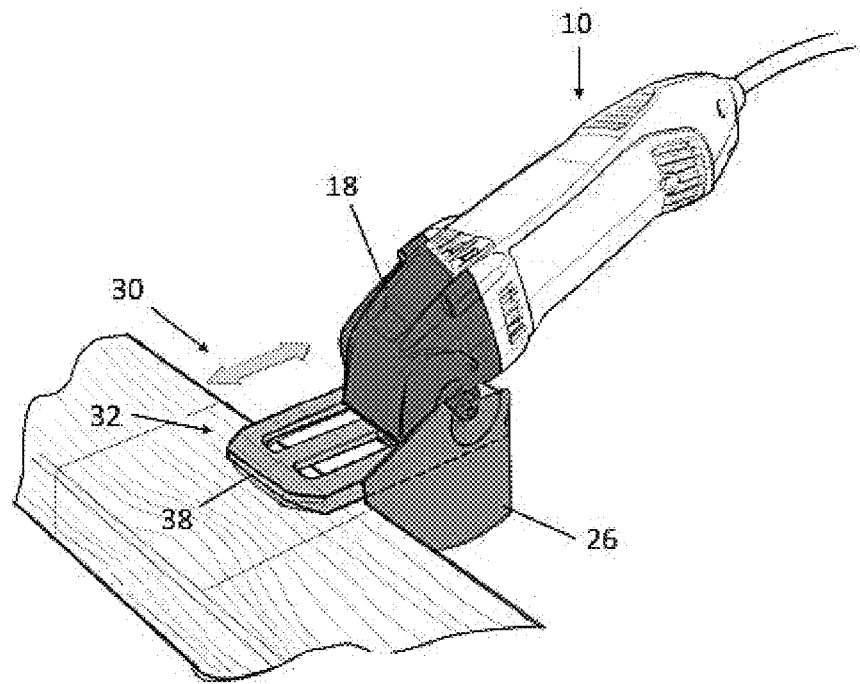
FIGS. 7a-7e depict a seventh embodiment of a guide foot for an oscillating power tool
Figure 7B:
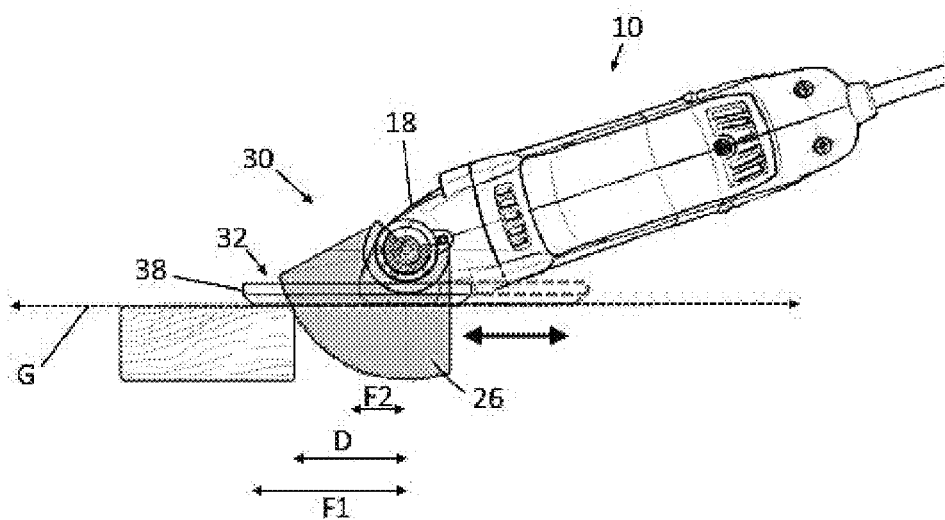
Figure 7C:
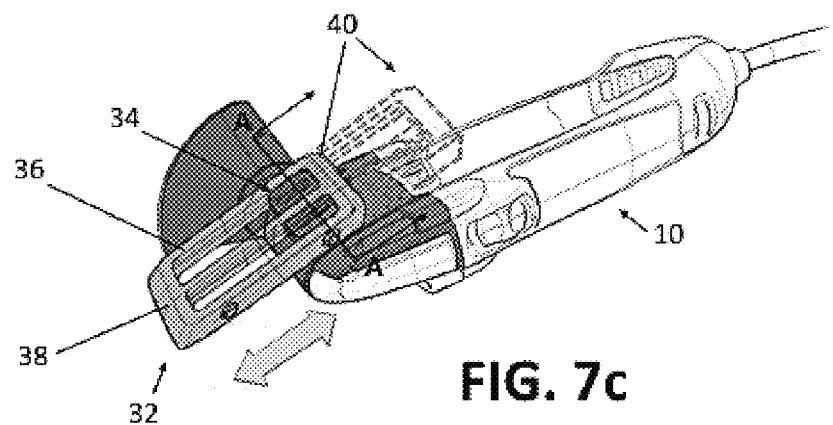
Figure 7D:
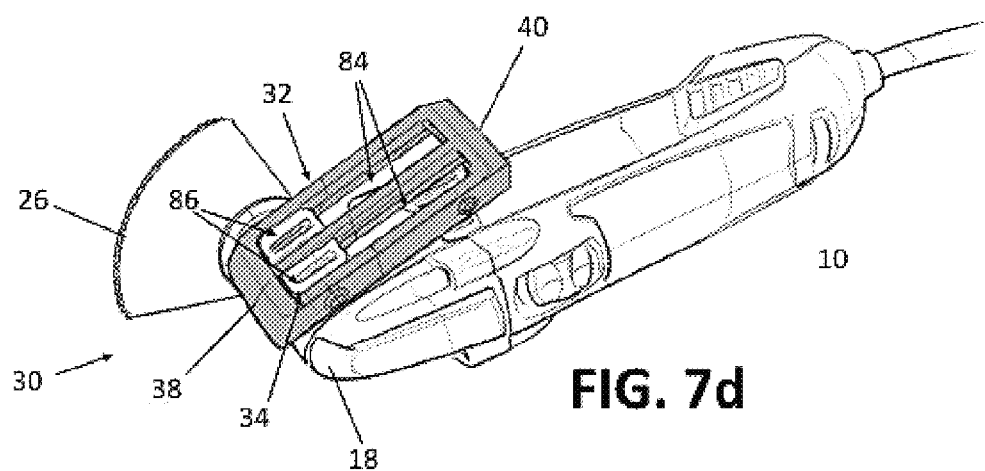

FIGS. 7a-7e depict an embodiment of a guide member that is configured to translate with respect to the housing between a stored position (FIG. 7d) and an extended position (FIG. 7a). In the extended position, the leading edge portion of the guide portion 32 is located the distance F1 from the oscillation axis which is greater than the distance D of the leading edge of the blade from the oscillation axis. In the retracted position, the guide portion 32 is translated rearwardly to a position at which the leading edge portion 38 is located a distance F2 from the oscillation axis which is less than the distance D.

Figure 7E:
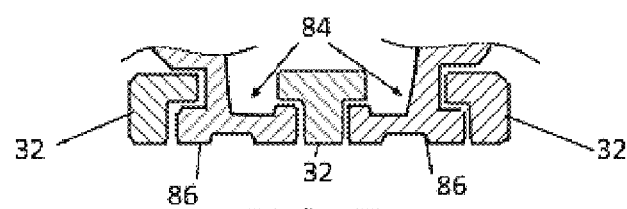

Translating/sliding movement may be enabled in any suitable manner. In the embodiment of FIGS. 7a-7e, the guide portion 32 includes slots or grooves 84 that extend between the leading and trailing edges 38, 40 of the guide portion 32. Referring to FIG. 7e, the attachment portion 34 comprises projections 86 which are attached to the nose portion of the housing which are slideably retained within the slots 84. In FIGS. 7a-7e, a pair of slots 84 and a pair of projections are provided for guiding the translating movement of the guide portion. In alternative embodiments, more or fewer slots and projections may be used.

The sliding guide foot 86 includes locking mechanisms 88 that enables the guide portion 32 to be locked in the extended and retracted positions. In one embodiment, the locking mechanisms 88 comprise spring loaded pins, or similar types of structures, that extend into the slots and are received in recesses provided in the guide structures 86. In alternative embodiments, any suitable type of locking or retaining mechanism may be used.

Figure 8A:
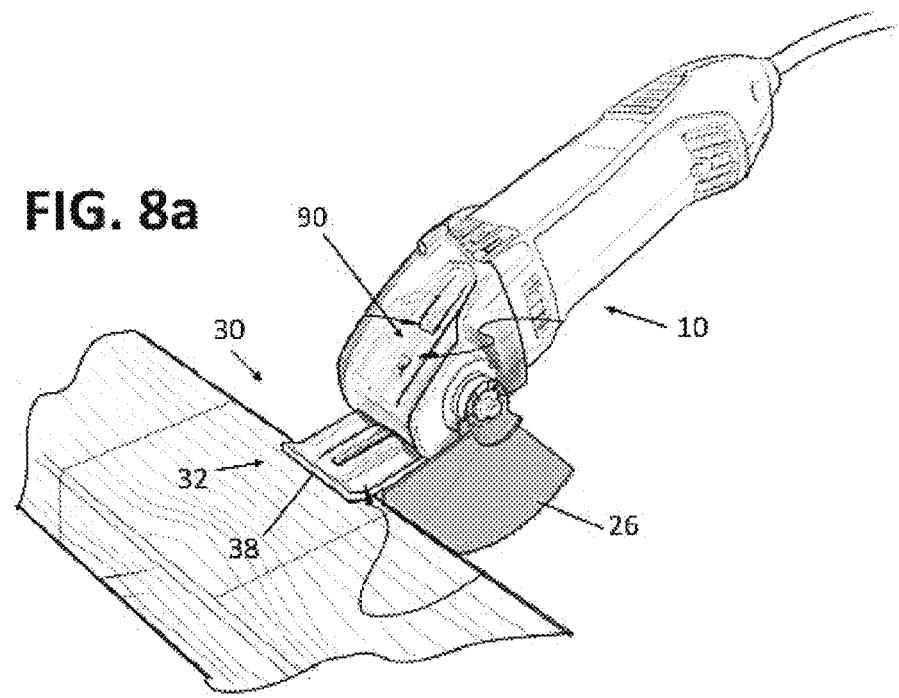
FIGS. 8a-8c depict an eighth embodiment of a guide foot for an oscillating power tool.
Figure 8B:
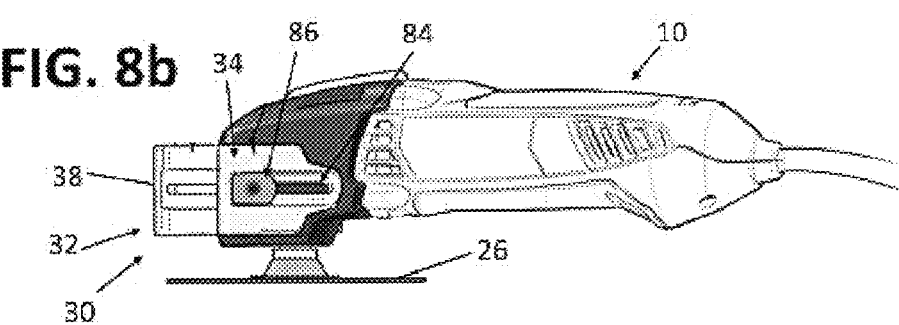
Figure 8C:
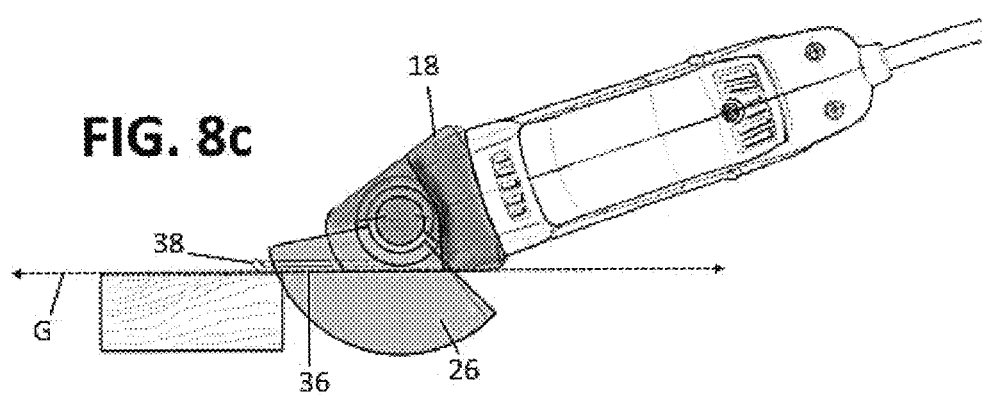

FIGS. 8a-8c depict another embodiment of a translating guide member for an oscillating power tool. In this embodiment, the guide portion 32 is translatably supported by an attachment member 34 that is configured to be removably attached to one or both sides of the nose portion 18 of the housing. The attachment member 34 includes a retaining structure (not shown). The nose portion 18 includes retaining features 90 which are configured to removably retain the attachment member 34 in an operable position on the housing. The retaining features 90 may be provided on both sides of the housing so that the guide member 30 can be used on either side of the tool 10.

Figure 9A:
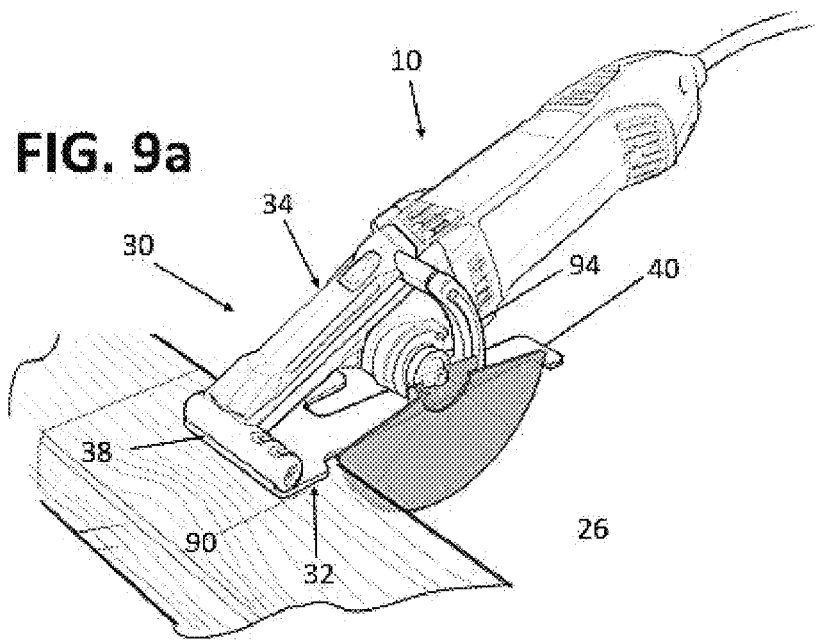
FIGS. 9a-9c depict a ninth embodiment of a guide foot for an oscillating power tool.
Figure 9B:
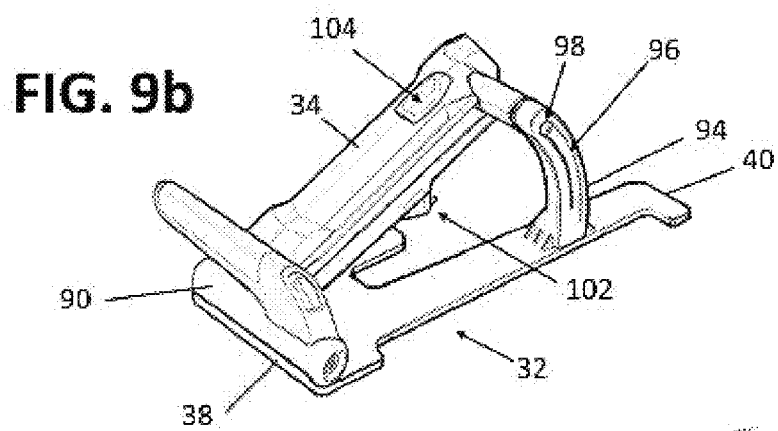
Figure 9C:
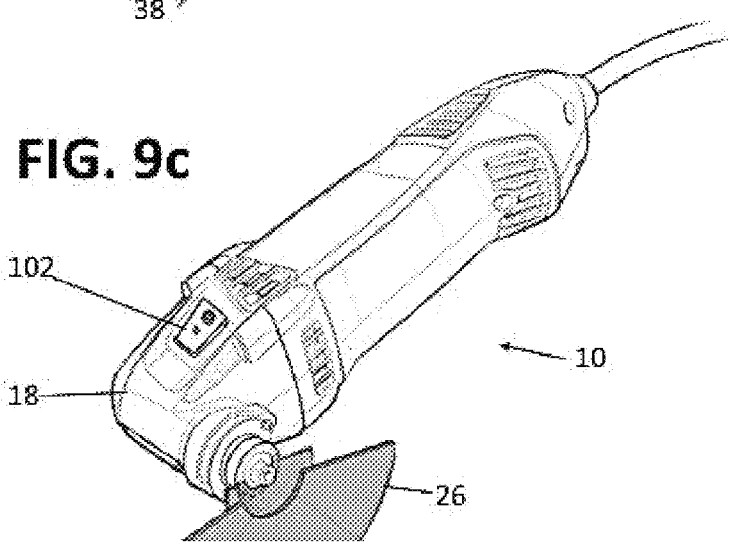

FIGS. 9a-9c depict yet another embodiment of a guide member for an oscillating power tool. In this embodiment, the guide portion 32 and attachment member 34 are also configured to provide a plunging movement for the oscillating tool. The attachment member is removably attached to the nose portion 18 of the tool housing. The guide portion 32 is similar in configuration to the guide portion of FIGS. 1a-1e. However, in this embodiment, the guide portion 32 is pivotably attached to the attachment portion 34 by a hinge 92 or similar type of structure located near the leading edge 38.

The guide portion 32 is configured to pivot with respect to the attachment portion 34 between a lower position and an upper position. The lower and upper positions are defined by a curved guide post that extends upwardly from the guide portion 32. The guide post 94 defines an arc-shaped slot 96 having a center of radius located at the pivot axis between the guide portion and the attachment portion 34. The attachment member has a projection 98 that extends through the slot 96. The slot 96 serves to guide the pivotal movement of the attachment portion 34 with respect to the guide portion between the lower position (corresponding to the bottom of the slot 96) and the upper position (corresponding to the top of the slot 96). The oscillation axis is moved closer to and farther away from the guide plane as the attachment portion 34 moves between the lower and upper positions. The projection 98 is configured to be releasably secured to the guide post at a plurality of positions along the slot 96 to define a desired depth for a cut which is based on the distance that the blade extends below the guide plane G.

The attachment portion 34 may be secured to the tool housing in any suitable manner. For example, the attachment portion may include a groove or slot in which at least a portion of the nose 18 portion of the housing is inserted. Complementary retaining features 102 on the nose portion 18 and on the attachment portion are then used to releasably retain the attachment portion 34 on the nose portion 18. The retaining features may have any suitable configuration and may be configured to be operated by a push button 104 or similar type of structure that enables the retaining features to be selectively coupled and uncoupled.

Figure 10A:
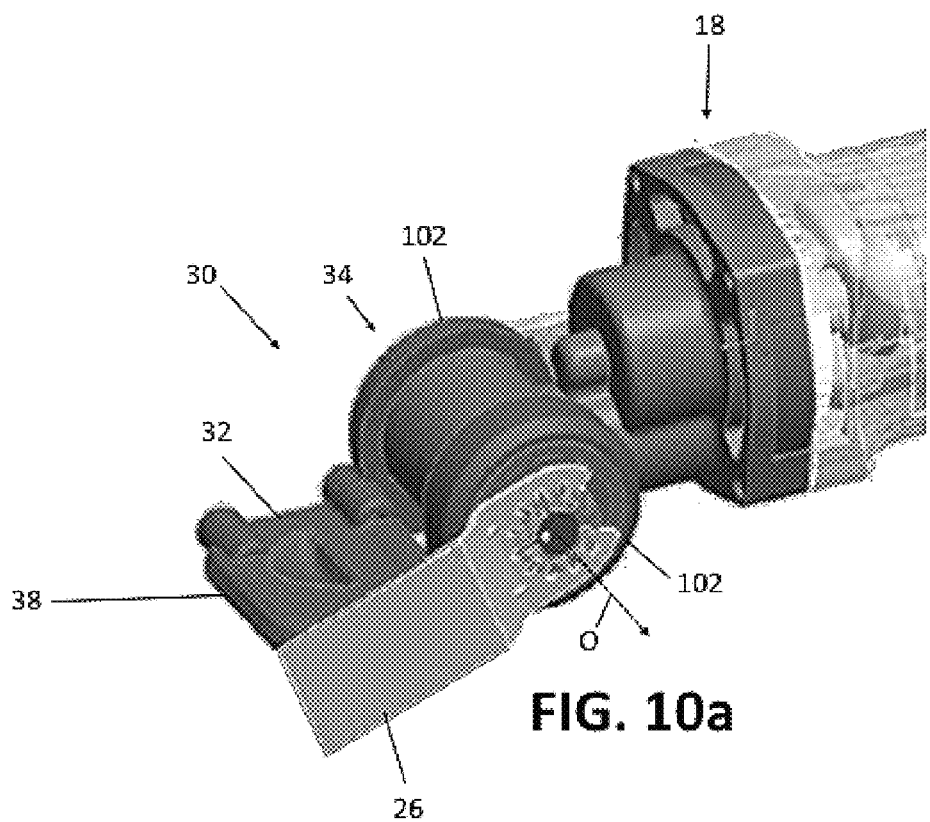
FIGS. 10a-10b depict a tenth embodiment of a guide foot for an oscillating power tool.
Figure 10B:
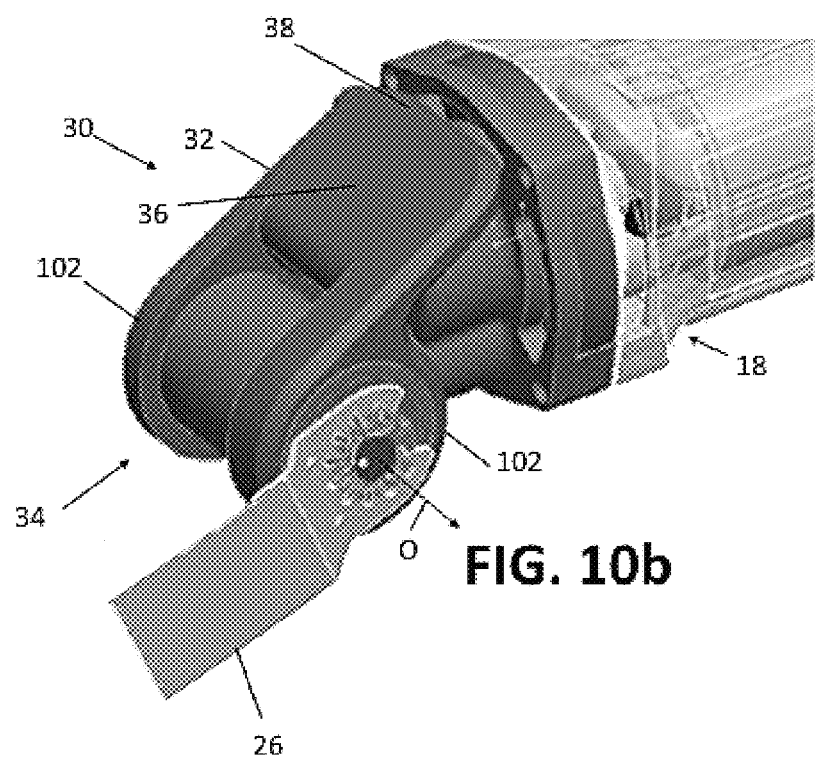

FIGS. 10a-10b depict alternate embodiment of a guide member 30 that is configured for pivotal movement with respect to the housing. The guide member 30 of FIGS. 10 and 10b includes a guide portion 32 having a surface 36 and an attachment portion 34 having two collar portions 102 which are pivotally attached to the nose portion 18 of the housing. The collars 102 each define an opening with a predetermined peripheral shape. The neck portion of the tool 10 is provided with an outer perimeter that is shaped complementary to the periphery of the opening to enable the collars 102 to be installed by aligning the peripheral shapes of the opening and the neck so that the neck can be inserted through the opening until the collars are situated around the neck portion.

The collar portions 102 are configured to be selectively rotated with respect to the nose portion about the oscillation axis O to a plurality of angular positions with respect to the oscillation axis. The guide member is configured to pivot with respect to the housing between an extended position (FIG. 10a) and a stored position (FIG. 10b). In one embodiment, an optional locking mechanism (not shown) for releasably locking the collar portions at any one of the plurality of angular positions is provided. The locking mechanism may comprise a spring-loaded button, or similar type of structure, that is configured to move a key on the collar into and out of engagement with recesses in the nose portion of the housing that define the plurality of angular positions.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A power tool comprising:
   a housing including a nose portion;
   a motor supported within the housing;
   an oscillating drive assembly coupled to the motor and configured to be driven to oscillate by the motor;
   a tool holder secured to the oscillating drive assembly and configured to removably retain an accessory tool so that the accessory tool is oscillated about an oscillation axis by the oscillating drive assembly, the tool holder being located exterior to the nose portion of the housing; and
   a guide member attached to the housing, the guide member including a leading edge portion, a trailing edge portion, and a planar guide surface that extends from the leading edge portion to the trailing edge portion,
   wherein the guide member is pivotably attached to the nose portion of the housing for pivotal movement about the oscillation axis with respect to the nose portion of the housing and with respect to the accessory tool when the accessory tool is retained by the tool holder between a stored position at which the leading edge portion of the guide member extends rearwardly adjacent the housing and an extended position at which the leading edge portion extends forwardly away from the housing, and
   wherein the guide member includes a locking mechanism configured to releasably lock the guide member at any one of a plurality of angular positions on the nose portion.

2. The power tool of claim 1, wherein the guide surface is configured to be placed in contact with a surface of a workpiece, the guide surface defining a guide plane that is substantially parallel to the oscillation axis.

3. The power tool of claim 2, wherein the guide member is removably attached to the housing.

4. The power tool of claim 3, wherein the guide member includes a collar portion that is pivotably attached to the nose portion of the housing for pivotal movement about the oscillation axis.

* * * * *